United States Patent [19]

Pearsall

[11] Patent Number: 4,591,385

[45] Date of Patent: May 27, 1986

[54] DIE MATERIAL AND METHOD OF USING SAME

[75] Inventor: Jeannine A. Pearsall, Spring Valley, N.Y.

[73] Assignee: Aremco Products, Inc., Ossining, N.Y.

[21] Appl. No.: 617,116

[22] Filed: Jun. 4, 1984

[51] Int. Cl.$^4$ ................................................ B28B 7/28
[52] U.S. Cl. .................................. 106/38.3; 106/38.9; 164/528; 264/16
[58] Field of Search ................. 106/286.4, 286.6, 38.3, 106/85, 35, 38.9; 433/199; 264/16; 164/528

[56] References Cited

U.S. PATENT DOCUMENTS

| | | | |
|---|---|---|---|
| 2,209,035 | 1/1939 | Prosen | 501/111 |
| 2,835,618 | 5/1958 | Keller et al. | 148/6.15 R |
| 3,649,732 | 3/1972 | Brigham et al. | 106/85 |
| 3,960,580 | 6/1976 | Stierli et al. | 106/85 |

*Primary Examiner*—Lorenzo B. Hayes
*Attorney, Agent, or Firm*—John F. Ohlandt

[57] ABSTRACT

A die material particularly suitable for the making of castings or the like, comprises 50 to 80 parts of magnesium oxide, 10–40 parts of alumina, 2 to 6 parts of monohydrated ammonium phosphate, and 1 to 4 parts of dihydrated ammonium phosphate. The dry blend thus formed, when mixed with a chilled liquid binder containing a collodial silica sol of about 40 weight percent solids content in the ratio of one portion of the liquid binder and from 2 to 5 portions of the dry blend, forms a ceramic slurry which can be readily set in hot water within 4 to 10 minutes. The set ceramic casting is then dry heated to about 250° F. for one to two hours. Molten metal is then applied on the casting for forming a metal jacket to use in dental prostheses.

4 Claims, No Drawings

DIE MATERIAL AND METHOD OF USING SAME

BACKGROUND OF THE INVENTION

1. Field of the Invention

The present invention relates generally to die materials used in the preparation of refractory castings, and particularly to such a material which, when mixed with a liquid binder, provides an easy flow, quick-setting castable ceramic slurry composition.

2. Background Information

Dry blends for use in the preparation of high temperature castable compositions are known from, for example, U.S. Pat. Nos. 2,209,035 to E. M. Prosen and 3,649,732 to K. Brigham et al. The known compositions generally include di-hydrated ammonium phosphate mixed with silica or glass, and magnesium oxide.

The prior compositions, however, required relatively long time periods for setting of typically from 20 to 30 minutes. Moreover, in actual practice with such prior compositions, the finished casting cannot be removed from a mold for a minimum of one hour, followed by a slow firing schedule (typically 200° F./hour to 1800° F.) to produce maximum strength for the casting.

SUMMARY OF THE INVENTION

An object of the present invention is to overcome the above and other problems in the known die materials.

Another object of the invention is to provide a dry blend which, when mixed with a suitable liquid binder, will provide a ceramic slurry which is capable of easy flow and quick setting.

Yet another object of the invention is to provide a method useful for making dental prostheses, according to which a ceramic casting for the purpose can be molded in a minimum of time because of the quick setting ability of the ceramic slurry composition; yet a fine detail, high strength, high temperature resistant, casting will result.

Another object of the invention is to provide a die material which, although well suited for use as a dry blend in the making of ceramic castings for dental purposes, may also be used for electrical insulators, heat-resistant components or the like.

According to one aspect of the present invention, a die material includes 50–80 parts by weight of magnesium oxide, 10–40 parts by weight of alumina in particulate form, 2–6 parts by weight of mono-hydrated ammonium phosphate, and 1 to 4 parts by weight of di-hydrated ammonium phosphate. Up to 25% silica can be included if desired.

It should be noted here that the inclusion of the mono-hydrated ammonium phosphate in the prescribed proportion, is the key factor in producing the high strength and fast setting characteristics of the castings obtained by the present invention.

In accordance with another aspect of the invention, a method of making a casting includes the steps of forming an impression mold, providing a dry blend comprising 50 to 80 parts by weight of magnesium oxide, 10 to 40 parts by weight of alumina, 2 to 6 parts by weight of mono-hydrated ammonium phosphate, and 1 to 4 parts by weight of di-hydrated ammonium phosphate; then, chilling a liquid binder comprising a colloidal silica sol to about 55° F., and blending together one portion by weight of the chilled liquid binder and from 1 to 5 portions by weight of the dry blend, proportioned as indicated above, thereby forming a ceramic slurry. The method further includes pouring the ceramic slurry into the mold, and placing the slurry-filled mold into a hot water bath whereby the slurry is allowed to set for about 4 to 10 minutes.

DESCRIPTION OF THE PREFERRED EMBODIMENTS

The present invention includes the preparation of a dry blend, and the mixing of the dry blend with a liquid binder such as a material known under the trade name "Ludox" which is a colloidal silica solution of about 40 weight percent solids content. Preferably, the liquid binder used in the present invention comprises about 99.9 parts by weight of the "Ludox" material and about 0.1 parts by weight of a suitable defoamer.

Prior to casting a ceramic die according to the present invention, it is preferred that an impression mold be coated with a surface tension agent, comprising about 95 parts by weight of isopropanol and about 5 parts by weight of a surfactant such as Triton X-100. It has been discovered that the pre-coating of the interior surface of the impression mold with the foregoing surface tension agent serves to reduce surface tension in the molds and thus permits a void-free casting. The precoating with the surface tension agent eliminates the need for a vibrator to reduce bubbles or voids, and enhances the flowability of the ceramic slurry of the invention and the ability of the slurry to creep into intricate shapes in the mold.

Moreover, since molten metal is usually applied on the finished ceramic castings to form a metal part or matrix, facile removal of the metal part after its solidification, without damaging either the ceramic or the metal, is necessary. It has been discovered that a parting agent comprising about 95 parts by weight of varnish and about 5 parts by weight of mica, when brushed on the ceramic casting and allowed to air dry prior to kiln heating the casting, enables the metal part to be easily removed after it solidifies on the casting.

By way of example and without intending to limit the scope of the present invention, the following specific examples are provided for further illustration of the present invention.

EXAMPLE I

A dry blend is prepared from the following materials by weight:

MgO (Periclaise fused Magnorite): 69%
Tab. Alumina (325 mesh): 23%
Mono-Hydrated Ammonium Phosphate: 5.5%
Di-Hydrated Ammonium Phosphate: 2.5%

In making the dry blend, it is essential, first, to ball mill the blend of mono hydrated and di hydrated ammonium phosphate to get a fine powder. At that point, the thus formed fine powder is mixed with the other constituents: MgO, Alumina (and silica if desired) in a blending-type mixer for a time sufficient to produce uniformity of blending. This procedure must be followed to have the necessary reaction when the liquid binder is added to the dry blend.

A liquid binder is prepared from the following materials by weight:

Ludox: 99.9%
Defoamer: 0.1%

The liquid binder is then chilled to about 55° F. A surface tension reducing agent is applied to an impression mold, any excess being shaken off.

One portion by weight of the chilled liquid binder is then mixed with 3.75 portions by weight of the dry blend and, after being thoroughly mixed to form a ceramic slurry, the slurry mixture is poured into the cavity of the impression mold. The ratio of one portion of chilled liquid binder to 3.75 portions of dry blend can be varied somewhat. Thus the liquid binder can be varied from 1 to 5 portions.

The chilling of the liquid binder allows for an increased pot life for the ceramic slurry, instead of a relatively short setup of 1–2 minutes which would normally result with the described proportions of liquid binder and dry blend, were the liquid binder not chilled.

The mold filled with the ceramic slurry is placed in a hot water bath, precautions being taken not to wet the ceramic slurry prior to setting. The slurry is then allowed to set in the hot water bath for 4–10 minutes, and the ceramic casting thus formed is then removed from the mold.

A parting agent comprising 95 parts by weight of varnish and 5 parts by weight of mica is thoroughly mixed and then brushed on the ceramic casting after removal from the mold. The parting agent is allowed to air dry for about ten minutes, and the casting is then dry heated in a kiln at 250° F. for about one to two hours. Molten metal can then be applied to the ceramic casting and, after being allowed to solidify, is removed typically, for dental prosthesis, in the form of a metal jacket.

EXAMPLE II

The previous example, that is Example 1, is repeated, except the dry blend is prepared as follows by weight:
MgO: 60%
Alumina: 33.5%
Monohydrated: 4.5%
Dihydrated: 2.0%

EXAMPLE III

The previous examples are followed, except that the dry blend is prepared as follows:
MgO: 60%
Alumina: 32.5%
Monohydrated: 5.0%
Dihydrated: 2.5%

While the foregoing description represents the preferred embodiments of the present invention, it will be obvious to those skilled in the art that various changes and modifications may be made therein without departing from the true spirit and scope of the invention.

I claim:

1. A ceramic die for casting a dental prosthesis, produced by providing a composition comprising:
   one portion by weight of a liquid binder, comprising colloidal silica sol of about 40% solids content, and from one to five portions by weight of a dry blend, said blend consisting essentially of 50–80 parts by weight of magnesium oxide, 10–40 parts by weight of alumina not coarser than 100 mesh, 2 to 6 parts by weight of monohydrated ammonium phosphate, and 1 to 4 parts by weight of dihydrated ammonium phosphate forming the composition into the desired shape of the die and allowing same to set.

2. A die according to claim 1, in which said dry blend consists essentially of 69 parts by weight of magnesium oxide, 23 parts by weight of alumina, 5.5 parts by weight of monohydrated ammonium phosphate, and 2.5 parts by weight of dihydrated ammonium phosphate.

3. A die as defined in claim 1, in which the particulate size of said alumina is about 325 mesh.

4. A die according to claim 2, in which the particulate size of said alumina is about 325 mesh.

* * * * *